(12) United States Patent
Wolfbeis et al.

(10) Patent No.: US 7,067,275 B2
(45) Date of Patent: Jun. 27, 2006

(54) BIOANALYTICAL MEASURING METHOD FOR DETERMINING CATALASES AND PEROXIDASES, AS WELL AS CONJUGATES, SUBSTRATES, ACTIVATORS AND INHIBITORS THEREOF

(75) Inventors: Otto S. Wolfbeis, Regensburg (DE); Meng Wu, Regensburg (DE); Zhihong Lin, Regensburg (DE)

(73) Assignee: Active Motif Chromeon GmbH, Tagernheim (DE)

( * ) Notice: Subject to any disclaimer, the term of this patent is extended or adjusted under 35 U.S.C. 154(b) by 378 days.

(21) Appl. No.: 10/292,388

(22) Filed: Nov. 11, 2002

(65) Prior Publication Data

US 2003/0124639 A1 Jul. 3, 2003

(30) Foreign Application Priority Data

Nov. 12, 2001 (DE) ................................ 101 55 160

(51) Int. Cl.
*C12Q 1/26* (2006.01)
*C12Q 1/00* (2006.01)
*C12N 9/02* (2006.01)
*G01N 33/53* (2006.01)
*G01N 33/20* (2006.01)

(52) U.S. Cl. ........................... 435/25; 435/4; 435/7.72; 435/189; 436/82

(58) Field of Classification Search .................... 435/4, 435/7.4, 7.72, 7.92, 25, 189, 968; 436/82; 423/263
See application file for complete search history.

(56) References Cited

U.S. PATENT DOCUMENTS 5,958,715 A 9/1999 Muller

FOREIGN PATENT DOCUMENTS

EP 1 239 049 A2 9/2002

OTHER PUBLICATIONS

Eleftherios P. Diamandis et al., "Multiple Fluorescence Labeling with Europium Chelators. Application to Time-Resolved Fluoroimmunoassays", Analytical Chemistry, American Chemical Society, Columbus, US, 61, 48-53 (1989).
Eva F. Gudgin Dickson et al., "Time-Resolved detection of lanthanide luminescence for ultrasensitive bioanalytical assays", Journal of Photochemistry and Photobiology, B: Biology 27, 3-19 (1995).
Evelyne Lopez et al., "Europium(III) Trisbipyridine Cryptate Label for Time-Resolved Fluorescence Detection of Polymerase Chain Reaction Products Fixed on a Solid Support", Clinical Chemistry, 39/2, 196-201 (1993).
Eleftherios P. Diamandis, "Streptavidin-Based Macromolecular Complex Labeled with a Europium Chelator Suitable for Time-Resolved Fluorescence Immunoassay Applications", Analytical Chemistry, 62, 1841-1845 (1990).
Andreas Oser et al., "Sensitive non-radioactive dot-blot hybridization using DNA probes labeled with chelate group substituted psorlen and quantitative detection by europium ion fluorescence", Nucleic Acids Research, 16:3, 1181-1196 (1988).

*Primary Examiner*—Jean C. Witz
*Assistant Examiner*—Susan Hanley
(74) *Attorney, Agent, or Firm*—Fulbright & Jaworski L.L.P.

(57) ABSTRACT

A bioanalytical method for determining catalases and peroxidases using europium ions.

19 Claims, 7 Drawing Sheets

BIOANALYTICAL MEASURING METHOD FOR DETERMINING CATALASES AND PEROXIDASES, AS WELL AS CONJUGATES, SUBSTRATES, ACTIVATORS AND INHIBITORS THEREOF

The invention concerns methods of determination using enzymes from the group comprising catalases and peroxidases and using optical indicators from the group comprising europium ligand complexes. The new method is based on the surprising finding that hydrogen peroxide ($H_2O_2$) bound by certain complexes of the europium (III) ion as a ligand is available for enzymatic reactions. The consumption of hydrogen peroxide by enzymes results in a change in the optical properties and in particular the luminescence-optical properties of the europium complexes. The new reagents allow an improved detection and determination of catalases and peroxidases as well as of substrates, inhibitors and activators thereof. Antigens and nucleic acid oligomers can also be detected or determined by using catalases or peroxidases as markers in immunological or genetic test methods.

The advantage of the indicators according to the invention is that they have a high selectivity, Stoke's shifts and long decay times. Hence it is possible to use a time-resolved measurement to firstly allow the interfering background fluorescence to decay and only afterwards to determine the fluorescence of the indicator EuTcHP, which is a complex of Eu, Tc and hydrogen peroxide, which results in extremely low detection limits in bioanalytics.

Enzymatic methods using catalases or peroxidases play an important role in bioanalytics. They are for example commonly used to qualitatively detect the presence of a certain enzyme or to quantitatively determine its activity. It is also possible to determine enzyme substrates in this manner. Finally inhibitors or activators of enzymes can also be determined by quantitatively determining the extent to which they retard or accelerate reactions. A review is given in the book *Enzymatic Methods of Analysis* by G. G. Guilbault, Pergamon Press, 1970.

Catalases are enzymes which degrade hydrogen peroxide ($H_2O_2$, referred to as HP in the following) as the first substrate. They are classed in group 1.11.1.6. of the enzyme catalogue. Peroxidases (POx) are enzymes which require a second substrate (e.g. a phenol) in addition to HP. They are classed in group 1.11.1.7, of the enzyme catalogue. Phenol-like compounds are typical substrates for peroxidases.

Catalases play an important role in the decomposition of the cell toxin HP and in cell regulation e.g. in apoptosis. Their activity can be determined by monitoring the decomposition of HP over time at 240 nm but this is almost impossible in vivo due to the very strong self-absorption of all biological material at this wavelength. Simple alternative direct methods are not known.

Peroxidases (as such or as markers in immunocomplexes or in an ELISA) can be visualized in various ways but this is almost always based on the consumption of HP by peroxidases or the formation of coloured or fluorescent products with their substrates. Hence the activity of a peroxidase can be optically detected by measuring the consumption of HP or the formation of coloured products.

Peroxidases also play an important role as markers in immunological methods of detection. These have become well-known under the name ELISA (enzyme-linked immunosorbent assay). Typically a peroxidase is bound as a marker to an antibody. When a complex is formed from the antigen and antibody, the POx contained therein can be detected by measuring the enzymatic activity. Methods based on a similar principle are also known for detecting a hybridization reaction between two nucleic acid strands.

Furthermore peroxidases which form insoluble coloured products with substrates (e.g. 4-chloro-1-naphthol) are used in immunoblotting since the coloured end-product allows a simple (visual) detection of an immunological reaction. Finally peroxidases are also used as markers in histochemical detection methods since the products formed with certain substrates, e.g. 3-amino-1-ethylcarbazole, can be readily visualized in histology.

Hence one can state that the analytics of catalases or peroxidases is extremely important for biochemical detection and determination methods.

Catalase analytics have previously commonly been carried out as follows. Catalase decomposes HP which results in a decrease in its strong absorption at 240 nm. The rate of decrease of the absorption is a direct measure for the current activity of catalase. This method is impractical and can only be used in solutions that have a low self-absorption at 240 nm which is seldom the case. Catalase can also be determined by determining the retarding effect of catalase on the formation of coloured products of HP and a substrate such as aminosalicylic acid (or another phenol) under the influence of a peroxidase. Since catalase decomposes the HP, the reaction slows down continuously. This method is also tedious.

The method presented here is much simpler. It is based on the addition of a strongly fluorescent complex consisting of the Eu (II) ion, an organic ligand in particular a β-dicarbonyl compound and hydrogen peroxidase (HP). This complex is converted by catalase with the consumption of HP into a complex (without HP) which has a considerably weaker fluorescence. The rate of the reaction can be monitored fluorometrically by excitation at 350–430 nm and measurement of the fluorescence at >600 nm.

Organic reagents have previously been commonly used to determine peroxidase. Optical methods of determination for peroxidases (POx) are based on the irreversible oxidation of certain organic substances to form coloured or fluorescent products. The POx substrates o-dianisidine, o-phenylene diamine, pyrogallol, azino-bis(3-ethyl-benzthiazoline-6-sulfonic acid (ABTS™) are commonly used. They all form strongly coloured products with peroxidase that can be measured photometrically.

Some phenols yield fluorescent dimers with HP in the presence of peroxidase (Y. Hayashi et al., *Anal. Chim. Acta* 1986, vol.186, p.131 et seq.) that exhibit a light blue fluorescence under UV light. A recent reagent of this type is homovanillic acid as reported by Wang, Schuber & Renneberg in *Sensors & Actuators* B28 (1995) 3–7. Unfortunately all biological materials have a strong self-fluorescence when excited with UV light. In *Analytical Biochemistry* 253 (1997) 162 Zhou et al. describe a stable non-fluorescent derivative of resofurin (Amplex Red) that can be converted by the enzyme peroxidase into a green fluorescent product and can be used to determine the activity of peroxidases.

The new method described here is superior to the prior methods since it is based on the addition of only one reagent i.e. a complex of Eu, an organic ligand e.g. tetracycline (Tc) and HP i.e. for example a system of EuTc and HP. The HP in this strongly fluorescent system is available for enzymatic oxidation and the complex EuTcHP is converted by catalase or peroxidase into the much less strongly fluorescent EuTc complex. Hence the activity of a catalase or POx can be simply detected by measuring the decrease of the fluorescence of the complex EuTc HP.

Generally, analysis of peroxidase using reagents from the group comprising europium reagents is known. The advantages of using Eu reagents are their large Stoke's shift and long decay times (which allows a time-resolved measurement). In the DE unexamined laid-open patent application 198 13 247.6 (1998) and in *Analyst* 125 (2000) 1537–1538 Meyer and Karst disclose a method for determining glucose using the enzymes horseradish peroxidase and glucose oxidase (GOx) and the reagents p-hydroxyphenylpropionic acid and Tb(EDTA). Its fluorescence decays considerably more slowly than the background fluorescence of many biological specimens.

Glucose was for example determined by adding glucose oxidase (GOx) as the first reagent to the solution to be examined followed by p-hydroxyphenylpropionic acid (pHPPS) as the second reagent and the enzyme peroxidase as the third reagent. The HP formed by the oxidase reacts under the influence of the peroxidase with the pHPPS to form a dimer which then forms a luminescent complex with a fourth reagent (a lanthanide ion), the fluorescence of which is amplified by adding the fifth reagent (caesium chloride). This method is very sensitive but cumbersome due to the need to use five reagents.

Lanthanide complexes were also used as markers in immunological tests. Certain trivalent ions of the lanthanoid elements can be used as covalent markers in luminescent immunological tests. In a method named DELFIA™, the antibody is labelled with a non-fluorescent lanthanoid ion and, after formation of the immunological complex, is admixed with two reagents (chelator and micelle former) which results in a considerable increase in the fluorescence intensity. The method was described by I. Hemmilä in a review article entitled *Progress in Delayed Fluorescence Immunoassays* which was published in the book *Fluorescence Spectroscopy: Methods & Applications* (Wolfbeis, O. S., Ed.; Springer Verlag, Heidelberg, 1993, p. 259–265). Diamandis and Christopoulos also give a review in *Anal. Chem.* 62 (1990) 1149A.

In an alternative immunoassay the lanthanide ligand (e.g. the phenanthroline dicarboxylic acid BCPDA) is added via an avidin-biotin binding reaction, and then a solution of Eu(III) nitrate is added. After drying the fluorescence is measured. Evangelista et al. give a review in *Clinical Biochemistry* 21 (1988) 173. In recent methods europium-labelled nanoparticles (10 to 500 nm diameter) have also been used as markers.

A lanthanoid is used in all of these methods which can be regarded as a marker and has to be covalently linked to a protein. No covalent marker is used in the method according to the invention but rather a new reagent is added which is decomposed by a catalase or peroxidase. Moreover the new method is based on the determination of photoluminescence and not on the determination of chemiluminescence which for example occurs when using luminol together with peroxidases. In contrast to chemiluminescent methods, an excitation light source is always used in the new method which is able to emit light between 300 and 450 nm.

It is known that the europium (III) ion forms strongly fluorescent complexes with certain β-dicarbonyl compounds. This applies to a number of β-dicarbonyl compounds and for numerous chelating agents such as EDTA. Furthermore Y. Rakicioglu, J. H. Perrin and S. G. Schulman have recently reported in *J. Pharm. Biomed. Anal.* 20:397–399 (1999) that the analysis of the antibiotic tetracycline can be improved by oxidizing the Eu(III) ion in the tetracycline europium chelate with hydrogen peroxide (HP). Indeed it is possible to detect the antibiotic in this manner with a high sensitivity.

One object of the invention was to provide an improved and in particular a highly sensitive detection method for enzymes such as catalases or peroxidases.

This object is achieved according to the invention by a method for the qualitative or quantitative detection of an enzyme selected from catalases or peroxidases or a substrate, inhibitor or activator thereof in a sample, characterized in that (a) a reagent which contains a trivalent europium ion, at least one organic ligand of the europium (III) ion and hydrogen peroxide is added to the sample, (b) a substrate of peroxidase is optionally added to the sample and (c) the enzyme is qualitatively detected or quantitatively determined on the basis of the changes in the optical properties of the reagent used in (a).

It has been surprisingly found that chelates of the europium (III) ion with organic ligands in particular with certain β-dicarbonyl compounds can only have weakly bound the hydrogen peroxide (HP) since the added HP is surprisingly still available for enzymatic reactions in the products that are formed. Hence the HP can in no way have been consumed as an oxidizing agent as reported by Rakicioglu et al. According to the invention this finding is used to improve enzymatic analysis by means of the differences in the optical properties of the europium ligand complexes with and without HP.

Figure 1:
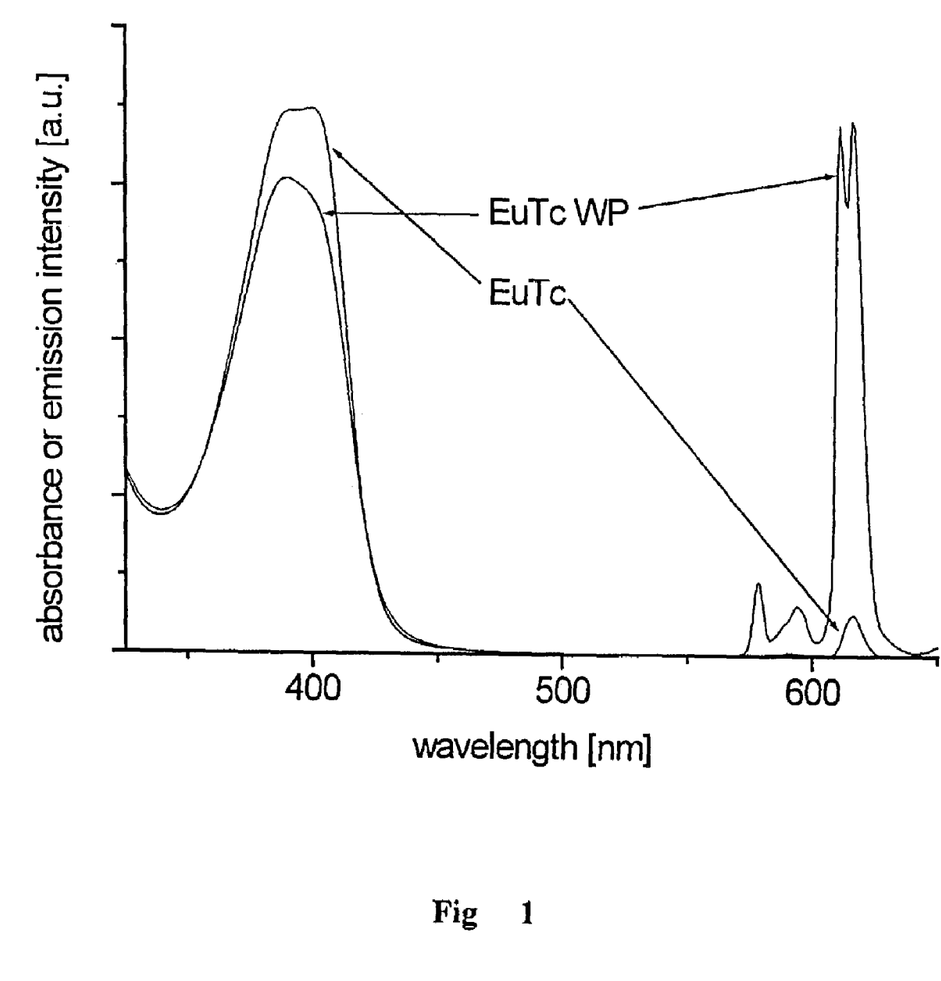
FIG. 1 shows the absorption and emission spectra of the complex consisting of the europium (III) ion, tetracycline and hydrogen peroxide (EuTcHP) before and after consumption of the hydrogen peroxide by a catalase or a peroxidase. The consumption of the hydrogen peroxide of the EuTcHP leads to the product EuTc. This has a greater absorption at 400 nm and also an almost 15-fold weaker emission intensity at ca. 615 nm.

The reagents according to the invention are formed by adding HP to the complexes of the europium (III) ion with organic ligands in particular with β-dicarbonyl compounds and have a considerably increased fluorescence intensity compared to the complexes without HP. This is shown in FIG. 1. Also the decay time of the fluorescence changes when HP is added: without HP the decay time of the EuTc complex is for example about 13 µs and about 9 µs in the presence of HP (i.e. in the EuTcHP complex).

The method according to the invention can be used for a qualitative test in order to determine whether an enzyme or its substrate, inhibitor or/and activator is present at all in a sample. It is, however, also suitable for quantitative determinations. The enzymes to be detected can be for example in a free, immobilized or conjugated form. The sample is preferably a solution to be examined in which case the reagent is added in a solid or dissolved form in step (a). The reagent is preferably a complex consisting of a trivalent europium ion, at least one organic ligand of the europium (III) ion and hydrogen peroxide. According to the invention the change in the optical properties of the added reagent are measured and in particular the change in the fluorescence-optical properties. For this purpose it is irradiated with light of an excitation wavelength of preferably between 300 and 450 nm and the fluorescence is determined at a second wavelength, the so-called measurement wavelength, of for example between 550 and 700 nm. In a particularly preferred embodiment the determination takes place after a certain initial delay time in particular of 1 µs to 500 µs, preferably 2 µs to 40 µs to allow the short-lived background fluorescence to decay and then the measurement is started. It is also possible to use a delay of 1 µs to 5 µs, preferably 2 µs to 4 µs. This measuring technique has the advantage that the short-lived background fluorescence can be almost completely excluded.

In the case of a peroxidase determination a peroxidase substrate is preferably also added to the solution.

Preferred embodiments of the invention are for example qualitative detection methods and quantitative determination methods for catalases in a free, immobilized or conjugated form as well as for their substrates, inhibitors and activators which are characterized in that (a) a solid or dissolved reagent which consists of a trivalent europium (III) ion, at least one organic ligand of the europium (III) ion and hydrogen peroxide is added to the solution to be examined, (b) the change in the optical and in particular fluorescence-optical properties of the reagent caused by a catalase are measured and (c) the catalase or substrates, inhibitors or activators thereof are qualitatively detected or quantitatively determined on the basis of the change in the optical properties of the reagent.

Other preferred embodiments are qualitative detection methods and quantitative determination methods for peroxidases in a free, immobilized or conjugated form as well as substrates, inhibitors and activators, which are characterized in that (a) a solid or dissolved reagent which consists of a trivalent europium ion, at least one organic ligand of the europium (III) ion and hydrogen peroxide is added to the solution to be examined, (b) a peroxidase substrate is optionally added to the solution, (c) the change in the optical and in particular fluorescence-optical properties of the reagent caused by a catalase are measured and (d) the peroxidase or substrates, inhibitors or activators thereof is qualitatively detected or quantitatively determined by means of the change in the optical properties of the reagent.

In a further embodiment the enzyme and in particular a catalase or peroxidase, is present conjugated to a biomolecule, preferably an antibody, an antigen, a DNA, an RNA or PNA or to a solid support.

The sample to be examined according to the invention is preferably a solution and in particular blood, serum, interstitial fluid, biological tissue, foods, drinks and precursors thereof, plant products, bioreactor liquids, cells or environmental samples.

The europium reagents according to the invention preferably have the following chemical but not necessarily stoichiometric composition:

in which

1. Eu represents a trivalent europium ion and Lig represents at least one ligand of the general chemical structure where
no more than two of the residues $R^1$, $R^2$ or $R^3$ can represent H, X represents OH, $NHR^4$, $NR^4_2$, $R^1$ to $R^3$ each independently of one another denote H, a linear, branched or cyclic, saturated or monounsaturated or polyunsaturated alkyl residue, a linear branched or cyclic, saturated or monounsaturated or polyunsaturated alkanoyl residue, an aroyl residue, $CF_3$, an optionally substituted alkyl residue or alkanoyl residue (suitable substituents e.g. are hydroxy, $C_1$–$C_6$ alkoxy, halogen or amino), OH, $NH_2$, alkylamino or dialkylamino, $R^4$ can represent H, alkyl or aryl where any of the residues $R^1$ to $R^4$ can be linked to one of the other residues $R^1$ to $R^4$ by means of an (optionally substituted e.g. with hydroxy, $C_1$–$C_6$ alkoxy, halogen or amino) carbocyclic or heterocyclic ring and 2. the molar ratio of Eu to Lig is between 30:1 and 1:5 and the molar ratio of Eu to HP is between 1:200 and 25:1.

The said alkyl residues or alkanoyl residues preferably contain 1 to 30 C atoms, in particular 1 to 8 C atoms and particularly preferably 1 to 4 C atoms. The said aryl residues or aroyl residues preferably contain 4 to 30, in particular 5 to 20 and particularly preferably 6 to 15 C atoms.

The molar ratio of Eu to Lig is preferably between 20:1 and 1:3 and the molar ratio of Eu to HP is preferably between 1:100 and 10:1.

The reagents obtained in this manner can be present in a solid or dissolved form. Preferred ligands are benzoylacetone, benzoyltrifluoroacetone, dibenzoylmethane, thenoyltrifluoroacetone, heterocyclic (ortho-hydroxy)carboxylic acids, aromatic or heterocyclic ortho-hydroxyketones and derivatives thereof, hydroxyquinones and partially hydrogenated and substituted hydroxyquinone-like compounds and anellated carbocycles including tetracycline and derivatives thereof.

A preferred reagent is the complex of the europium ion with tetracycline and hydrogen peroxide (EuTcHP). Its fluorescence intensity depends on the stoichiometry between the europium ion and tetracycline (typical range 10:1 to 1:10). The fluorescence of EuTcHP is substantially decreased when its Hp is consumed by catalases or peroxidases.

The method according to the invention enables the determination of various parameters that are related to enzymes. Thus it is possible to determine the activity of dissolved or conjugated enzymes from the group comprising catalases and peroxidases.

In order to detect catalases or peroxidases a reagent according to the invention is added to the system to be examined together with a substrate such as phenol in the case of peroxidase. Afterwards the decrease in the fluorescence is detected or monitored over time at an excitation wavelength of 330 to 430 nm, in particular 350 to 400 nm and at an emission wavelength of ca. 600 to 630 nm. Alternatively the decrease in the decay time can be determined.

Figure 2:
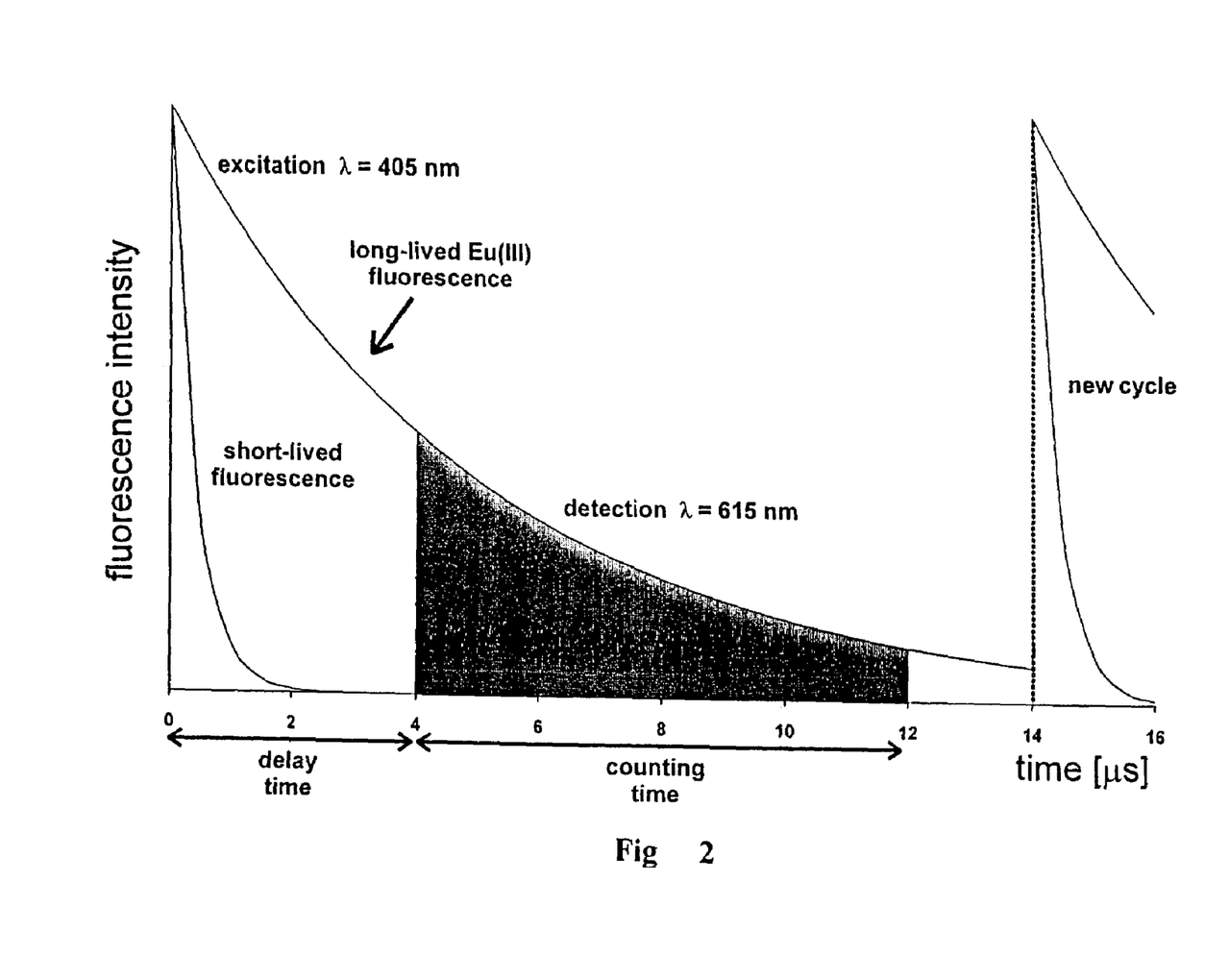

A quantitative determination can be carried out by measuring the kinetics of the reaction as shown in FIG. 2. This shows the change in the emission over time as a function of the activity of POx in the sample. Plotting the decrease of the emission per unit of time ($\Delta I/\Delta t$) against the added amount of POx results in a quantitative relationship.

The method is particularly important for simple tests for myeloperoxidase (MPOx). By determining this enzyme it is possible to differentiate acute myelocytic leukaemia from other types of leukaemia. The test has previously usually been carried out with reagents which lead to the formation of dark coloured precipitates (formed from HP under the influence of the POx). This drawback no longer occurs when using the method according to the invention.

The invention can also be used to determine substrates of peroxidases. Peroxidases accept HP as the second substrate. Thus for example phenol is oxidized by peroxidase (POx) according to the following reaction equation:

$$2C_6H_5OH+H_2O_2 \rightarrow C_{12}H_8(OH)_2+2H_2O$$

The concentration of phenol can thus be determined by measuring the consumed amount of HP. The determination is usually carried out kinetically i.e. the kinetics of the consumption of HP is monitored over time, typically for 1 to 5 minutes.

However, it is also possible to determine other substrates. Substrates that are not directly converted by catalases or peroxidases can also be determined by means of the indicators according to the invention i.e. when the substrate is firstly degraded by one or more other enzymes. The product resulting from this conversion is then a substrate for a catalase or oxidase and is further degraded by these with the consumption of HP. Typical enzyme cascades of this type are shown in the following:

phosphotyrosine (+tyr-kinase)→tyrosine
tyrosine (+tyrosinase)→DOPA
DOPA (+POx)+EuTcHP→dimer+EuTc Hence phosphotyrosine can be determined by means of a reagent according to the invention using a peroxidase. This specific example is particularly important in connection with the determination of inhibitors of tyrosine kinase.

The method according to the invention can also be used in immunoassays. Catalases and peroxidases are used in a conjugated form in optical immunological tests. In a typical method an antibody is labelled with a peroxidase. This is depicted by an asterisk in the following. If the antibody (Ab*) labelled in this manner finds a corresponding antigen (Ag), an Ag/Ab* complex is formed which also contains the POx marker.

In a typical sandwich assay an antibody is firstly immobilized. An antigen is bound to it. Labelled antibody Ab* is now allowed to dock onto the Ab/Ag complex that is formed:

The more Ag that is initially formed, the more Ab* binds to the first complex as a sandwich and forms a conjugate Ab/AgAb*. If the label (*) was POx, the unknown amount of Ag can be determined by determining the activity of POx in the Ab/Ag/Ab* complex. According to the invention a reagent is used to measure the activity of a catalase or peroxidase in an immunocomplex which contains Eu, an organic ligand and HP, in particular the reagent EuTcHP which in the case of POx additionally contains a substrate.

Labelling a DNA with a catalase or peroxidase allows a hybridization to be detected similar to the immunoassay and thus the method according to the invention can be used in hybridization assays. The enzymatic activity of the catalase or peroxidase on the DNA is determined by means of the reagents according to the invention via the consumed HP. In the case of catalase only the reagent (e.g. EuTcHP) needs to be added but no second substrate. In the case of peroxidase a second substrate (e.g. phenol) is required. The decrease in the fluorescence intensity over time or the increase in the decay time is monitored.

In the method according to the invention for detecting antigens or nucleic acid oligomers the reagent in step (c) is preferably added as a solid or dissolved reagent.

The invention is further elucidated by the following examples and attached figures.

FIG. 2 shows a schematic representation of a time resolved measurement for suppressing background fluorescence. It is excited at time 0 with a short light pulse, and then one waits until the short-lived background fluorescence has decayed. After this delay time (4 μs in the case of EuTcHP) the detection window (counting time) is opened until time 12 μs and the same cycle is repeated after 14 s. This measuring technique has the advantage of an almost complete suppression of the short-lived background fluorescence, but is only possible when the reagents have a fluorescence which decays considerably more slowly than all other materials.

FIG. 3: Enzymatic degradation of the complex of Eu(III), tetracycline and hydrogen peroxide (molar ratio 17:51:400) by added catalase (from bovine liver). The complex decays with consumption of HP to form EuTc which has a much weaker fluorescence. This results in a considerable decrease in the fluorescence to a level which corresponds to that of the EuTc complex. The more catalase is added the more rapid is the decay. The decrease in the fluorescence per unit of time serves as a measure for the activity of the dissolved enzyme or of the enzyme conjugated to a support. The activity in this case is stated in units per millilitre (U/ml).

FIG. 5 shows the result of an ELISA assay. The antigen IgG was immobilized on the bottom of a microtitre plate and reacted with various amounts of anti-IgG which was labelled with POx. After washing and adding the reagent EuTcHP, the peroxidase of the anti-IgG decomposes the reagent which results in a considerable decrease in the fluorescence intensity. The more labelled anti-IgG was added, the more rapidly did the decomposition occur. Curve (a) shows the time course in the absence of labelled anti-IgG. This component must be subtracted as a blank value. The added amounts of anti-IgG-POx were 0.3 ng/ml in (b); 0.6 ng/ml in (c); 3.0 ng/ml in (d); 6.0 ng/ml in (e) and 600 ng/ml in (f).

FIG. 7 shows a section of a 96-well microtitre plate in which a target oligomer (see example 6) was immobilized in the wells. Subsequently random 20-mer sequences were added to each well and in some wells the exactly complementary E-HEC sequence was added; all of the sequences were labelled with POx. This was followed by hybridization, washing and addition of the reagent EuTcHP and phenol. In the figure the bright zones represent strong fluorescence. This occurs at those positions at which there is no peroxidase and hence at which no E-HEC-POx had bound to the target. Dark zones indicate the presence of POx-labelled E-HEC at these sites which had degraded the added fluorescent EuTcHP into the weakly fluorescent EuTc.

EXAMPLES

Example 1

1.48 g of the buffer salt MOPS Na⁺ salt (Fluka AG) is dissolved in 490 ml distilled water, the pH of the solution is adjusted to pH 6.9 by adding a few drops of 70% perchloric acid and it is made up to 500 ml. The reaction solution is obtained by dissolving 4.0 mg tetracycline hydrochloride (Fluka AG), 0.1 ml hydrogen peroxide (30% solution; Merck) and 9.6 mg EuCl$_3$-hexahydrate (Alfa) in 100 ml of the above buffer. The reagent can be obtained in a dry form by preparing the dissolved reagent without the addition of buffer and then freeze-drying the solution. Other quantity ratios of tetracycline to europium ions are also possible.

Example 2

Determination of the Activity of Catalase

Figure 3:
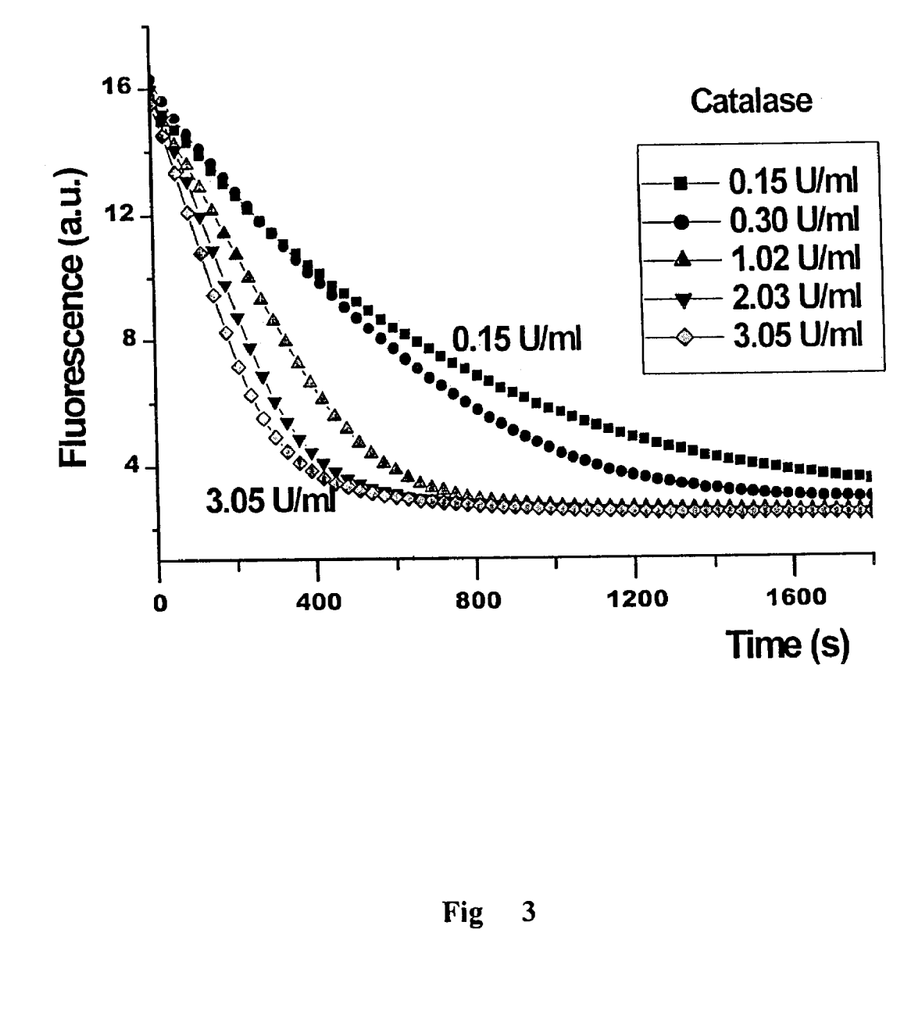
Figure 4:
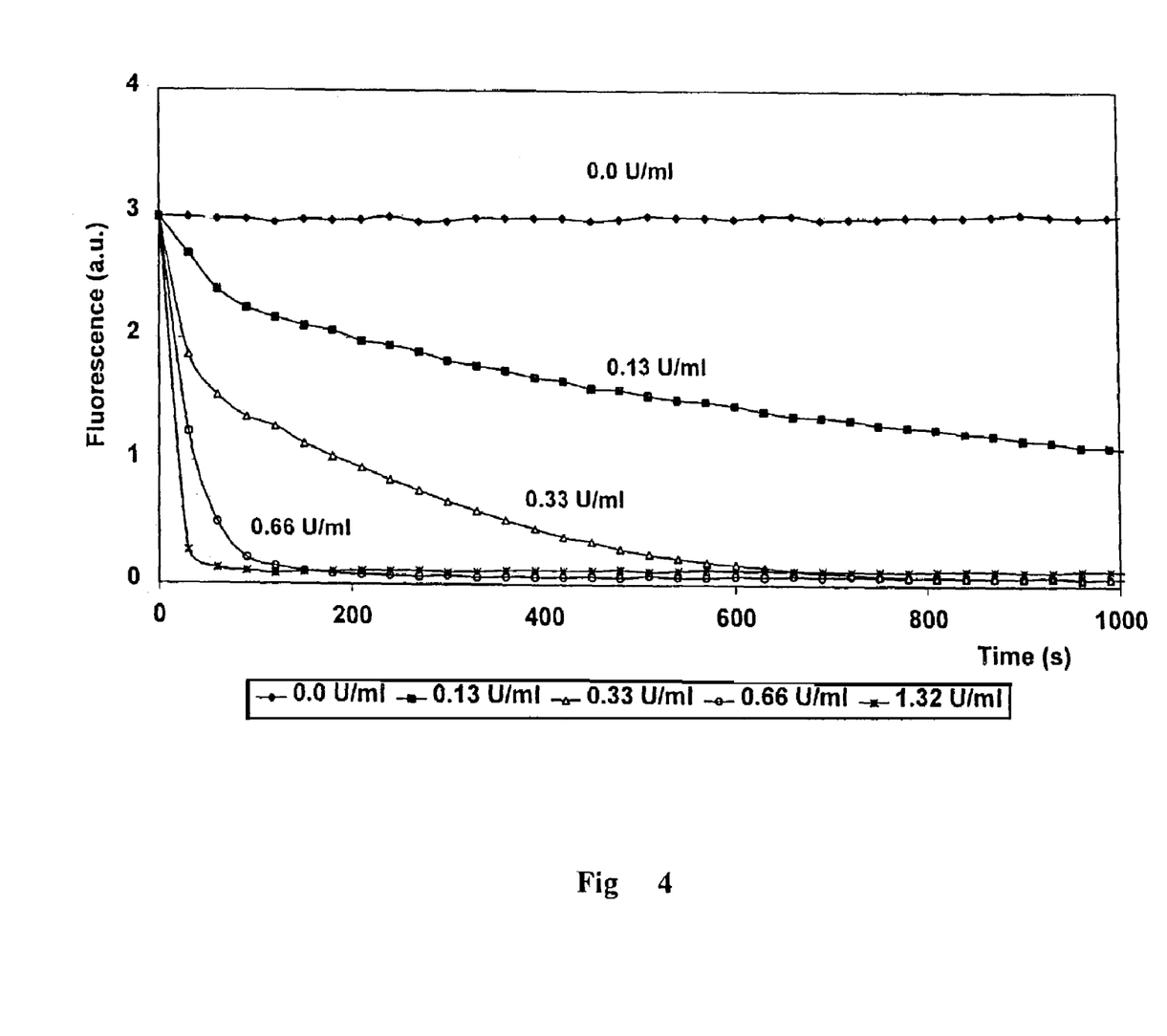
FIG. 4: Enzymatic degradation of the complex consisting of Eu(III), tetracycline and hydrogen peroxide ("EuTcHP") by adding the enzyme peroxidase and the substrate phenol. The hydrogen peroxidase-free complex which fluoresces only weakly is formed from the EuTcHP complex. Again the decrease in the fluorescence per unit of time serves as a measure for the activity (units/ml) of the dissolved or conjugated enzyme.
Figure 5:
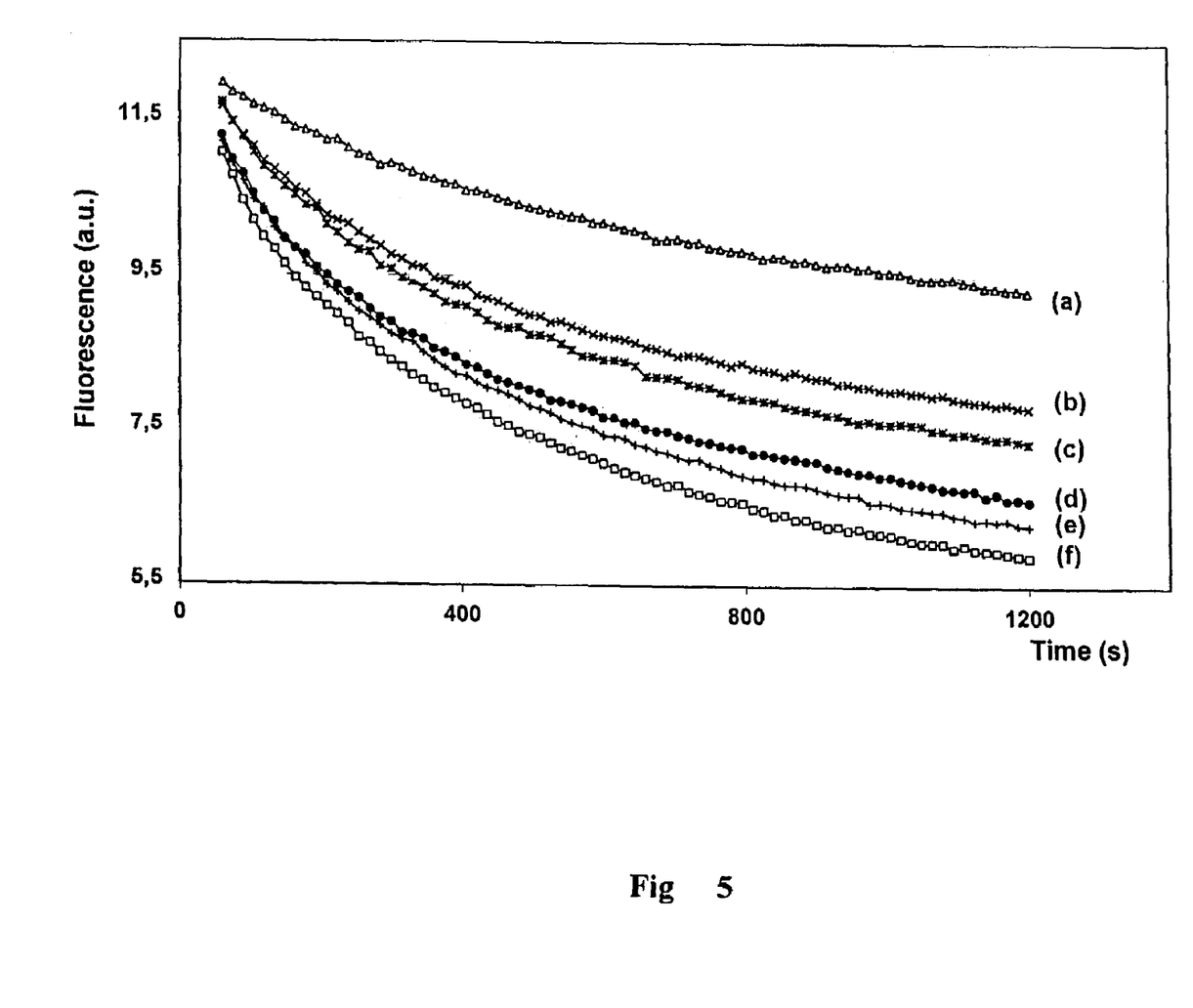
Figure 6:
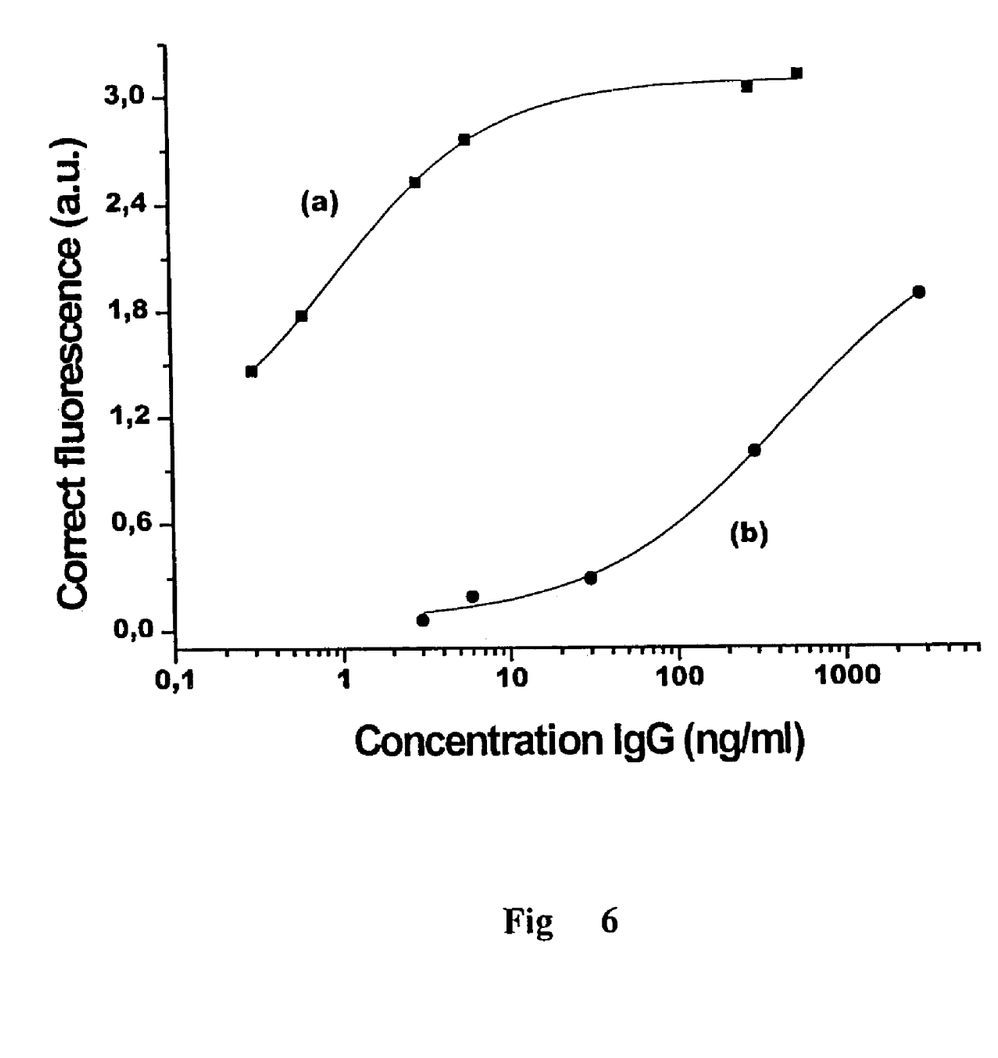
FIG. 6 shows calibration curves that are obtained by plotting the corrected fluorescence after a certain time versus the logarithmic concentration of IgG. Curve (a): calibration curve of a sandwich ELISA; (b) calibration curve of a direct ELISA. The sandwich ELISA for the IgG has approximately the same sensitivity as the most sensitive known detection methods (0.3 ng/ml).
Figure 7:
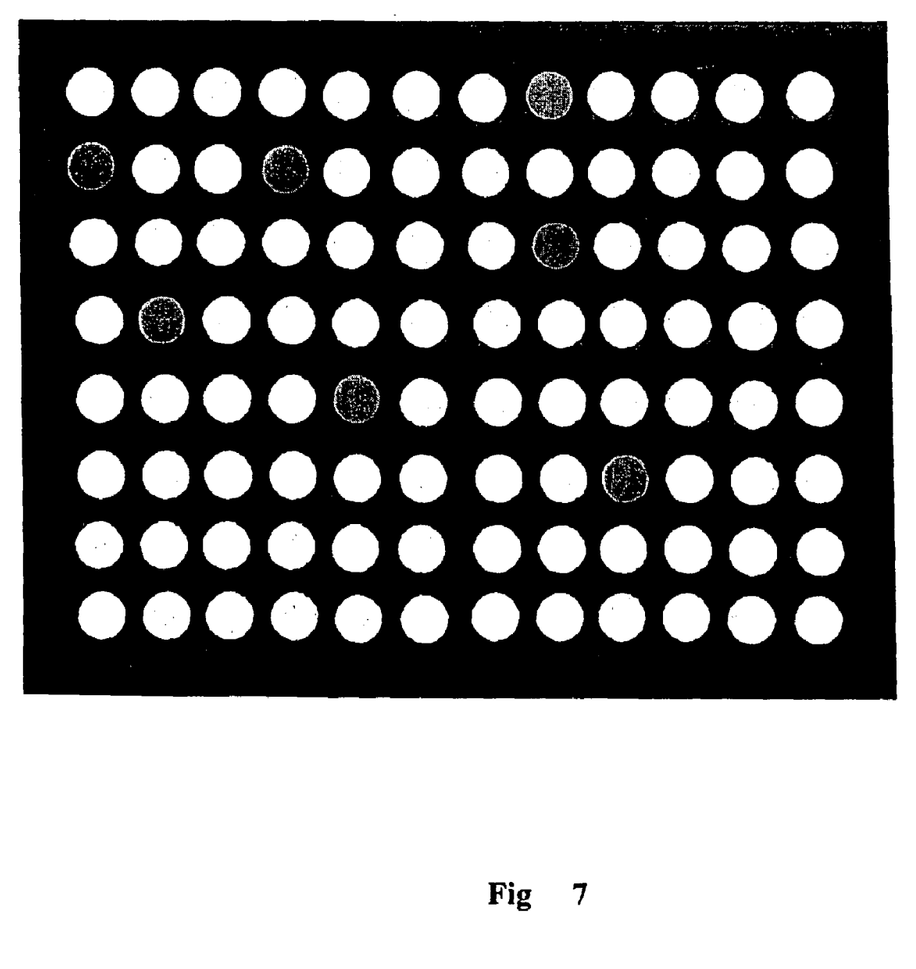

This determination is carried out by adding reagent from example 1 to a solution containing between 0.0 and 3.0 units/ml catalase. The kinetics of the decomposition of hydrogen peroxide in the EuTcHP is shown in FIG. 3. This is also used for the quantitative analytical evaluation.

Example 3

Enzymatic Determination of Phenol (a) Peroxidase stock solution: 1.0 mg POx (from horseradish; 1000 units/mg, product P-6782; from Sigma) in 10 ml MOPS buffer.

(b) Method of determination: The wells of a microtitre plate are filled consecutively with the following reagents: 0.2 ml of the solution to be analysed for phenol (with a content between 2 and 20 mg per litre), 0.01 ml of the reagent solution (see example 1) and finally 0.1 ml of the peroxidase stock solution. The decrease in fluorescence intensity is monitored over time starting when the POx is added. The increase in fluorescence after a defined time e.g. after 3 min is a measure for the concentration of phenol present in the sample. The exact value can be calculated from previously determined calibration curves.

In some microtitre plate reading instruments it is also possible to carry out a time-delayed measurement. For this a delay time of 1 microsec is set on the instrument (e.g. Ultra II, from TECAN; Crailsheim) and after this the emission intensity is integrated over 25 microsec before the next excitation pulse is triggered.

Example 4

Determination of Enzyme Inhibitors

Catalases and peroxidases are massively inhibited among others by heavy metal ions, sulfite and sulfide ions (H. Zollner, Enzyme Inhibitors; Wiley & Sons, 1996). The amount of consumed HP depends on the activity of the catalase or POx and can be determined with the aid of a reagent according to the invention. The retardation of the decomposition of the EuTcHP complex by catalase described in example 2 can be used to determine the concentration of such inhibitors.

Example 5

Determination of an Antigen (HSA) by an Immunoassay on Magnetic Particles (a) Biotinylation of anti-HSA: Polyclonal anti-HSA (goat; Sigma Prod. No. A-1151) was diluted 10-fold with phosphate buffer and then reacted with the biotinylation reagent biotinamidocaproic acid-sulfo-NHS ester (Sigma, B-1022) according to the instructions of Psantano & Kuhr in *Analytical Chemistry* 65 (1993) 623. The anti-HSA biotinylated in this manner was then bound to the magnetic particles (see below under (c)).

(b) Labelling of anti-HSA with POx: It was labelled by means of a biotin-streptavidin binding reaction. Polyclonal anti-HSA (goat; Sigma Prod. No. A-1151) was diluted 10-fold with phosphate buffer and then firstly labelled with streptavidin maleinimide (Sigma, Prod. No. S-9415) according to the instructions of Duncan et al. in *Analytical Biochemistry* 132 (1983) 68. The resulting streptavidin/anti-HSA conjugate was electrophoretically purified and then the POx-labelled reagent biotinamino-POx (Sigma No. P-9568) was added and it was electrophoretically purified.

(c) Immobilization of anti-HSA on magnetic beads: The immobilization was by means of a biotin-streptavidin binding reaction. 1 ml of a suspension of paramagnetic iron oxide particles with surface-bound streptavidin (d=1 μm; Sigma, Prod. No. S 2415) containing about 1 mg immobilized streptavidin) was admixed with 1 ml of a solution of biotinylated anti-HSA (see under (a)) and allowed to stand for 1 h at room temperature. The particles were then separated with the aid of a magnetic separator (Sigma, Prod. No. M-1292).

(d) Method of determination: The magnetic particles obtained according to (c) were suspended in 2 ml phosphate buffer pH 7.0 and admixed with solutions containing between 2 and 20 μg/ml HSA which corresponds to the HSA concentration which occurs in the urine or in microalbuminuria. After 10 min the particles were separated by a magnetic separator, resuspended in 2 ml PBS and admixed with a solution of 1 mg/ml of the POx-labelled polyclonal anti-HSA (see (b)). In such a sandwich assay the anti-HSA binds to the HSA that is already present on the particles. After another magnetic separation and resuspension the following reagents were added: 100 ml of a 0.1% solution of phenol in PBS; 1 ml of a solution which contains 17 μmol/l tetracycline (Sigma, Prod. No. T-3258), 51 μmol/l europium chloride (Fluka) and 400 μmol/l hydrogen peroxide (similar to the reagent of example 1).

The amount of HP consumed per unit of time can be determined from the decrease in fluorescence at 610 to 620 nm (with excitation at 405 nm) and is proportional to the concentration of HSA in the sample.

Example 6

Detection of a Specific Oligomeric Sequence by Means of a Hybridization Assay (a) Principle: The binding of a POx-labelled 15 mer to a complementary 15 mer which had been immobilized on an agarose particle was detected by means of the POx activity that can be detected using the reagents according to the invention. The sequence 5'-AAG-TAG-TCA-ACG-AAT-GGC-GA-3' ("E-HEC") was examined which is specific for those *E. coli* mutants (E-HEC) that are responsible for the food poisoning that is occasionally caused by infected beef.

(b) Preparation of an oligomer labelled with peroxidase

The 5' end of a 20 mer target having the sequence 5'-AAG-TAG-TCA-ACG-AAT-GGC-GA-3' was labelled with peroxidase ("E-HEC-POx"). The complementary oligomer (5'-TCG-CCA-TTC-GTT-GAC-TAC-TT-3') was labelled at the 5' end with biotin (Metabion GmbH, Munich). Afterwards the complementary ("COMP") oligomer was bound to streptavidin which was located at the bottom of a microtitre plate.

(c) Competitive hybridization and detection of the activity of POx on the bound oligomer. 10 μl of a solution of oligomer ("E-HEC") and of POx-labelled oligomer ("E-HEC-POx") were added to each well of the microtitre plate containing the immobilized COMP and hybridized at 55° C. The wells were emptied and washed. After adding 20 μl reagent (EuTcHP; see example 1) and 20 μl of a phenol solution, the decrease in fluorescence at 610 to 620 nm (with excitation at 405 nm) was monitored. The decrease in fluorescence of the EuTcHP was more pronounced when less E-HEC was present since most binding sites of the target have been occupied by E-HEC-POx. When POx-labelled sequences were used that are different to those of E-HEC or E-HEC-POx, there was no significant decrease in fluorescence due to the absence of hybridization.

Example 7

Example of a Time-resolved Measurement Procedure for EuTcHP

The fluorescence of the europium reagents according to the invention having the general composition EuTcHP decays relatively slowly but considerably more rapidly than for example complexes of Eu(III) that are used as covalent markers in the DELFIA immunological test. The measuring procedure and time domains are shown in FIG. 2. The fluorescence of the reagent is excited with a short pulse from a xenon lamp (0.1 to 1.5 μs), or from a blue (405 nm) or a UV light emitting diode (375 nm; Nichia). The emitted light intensity is then integrated after a delay time of 4 μs. The decay time of EuTcHP is 9 μs, the decay time of the reaction product EuTc is 13 μs.

The invention claimed is:

1. A method for detecting an analyte comprising:
   (a) adding a reagent comprising a trivalent europium ion, at least one organic ligand of the europium (III) ion and hydrogen peroxide to a sample containing an analyte selected from the group consisting of an enzyme, an enzyme labelled biomolecule, an enzyme inhibitor, an enzyme activator, and a substrate of a peroxidase, wherein the enzyme is selected from the group consisting of a catalase and a peroxidase;
   (b) wherein when for the detection of a peroxidase, a substrate of peroxidase is added to the sample; or wherein when the detection is for a substrate of a peroxidase, a peroxidase is added to the sample; and
   (c) qualitatively detecting or quantitatively determining the analyte on the basis of changes in luminescence-optical properties of the reagent used in (a).

2. The method of claim 1, wherein the enzyme is present conjugated to a biomolecule or to a solid carrier.

3. The method of claim 1, wherein the detection or the quantitative determination is carried out hi blood, serum, interstitial fluid, biological tissue, in foods or drinks, in plant products, in bioreactor liquids, cells or in environmental samples.

4. The method of claim 1, comprising measuring the reaction-retarding effect of said enzyme inhibitor on said luminescence optical change in the properties of the added reagent caused by a catalase or peroxidase is measured to obtain a value and using that value to detect the presence of the inhibitor or to determine the concentration of the inhibitor.

5. The method of claim 1 for detecting or determining inhibitors of the enzyme, wherein the method is used to screen the effectiveness of potential pharmaceutical agents as enzyme inhibitors.

6. The method of claim 1 for detecting or determining an activator of the enzyme, wherein the accelerating effect of the activator on the activity of catalase or peroxidase is determined and used to determine the concentration of the activator.

7. The method of claim 1, wherein said reagent has the formula:

wherein
Eu is a trivalent europium ion,
Lig is at least one organic ligand form the group comprising β-dicarbonyl compounds or enols thereof and $H_2O_2$ is hydrogen peroxide; wherein the molar ratio of Eu to Lig is between 30:1 and 1:5 and the molar ratio of Eu to hydrogen peroxide is between 1:200 and 25:1.

8. The method of claim 7, wherein the organic ligand is selected from the group consisting of benzoylacetone, benzoyltrifluoroacetone, dibenzoylmethane, thenoyltrifluoroacetone, heterocycic (ortho-hydroxy)-carboxylic acids, aromatic or heterocyclic ortho-hydroxyketones and derivatives thereof, hydroxyquinones and partially hydrogenated and substituted hydroxyquinone compounds, tetracycline and derivatives thereof.

9. The method of claim 1, wherein said biomolecule is an antigen or a nucleic acid oligomer which is visualized by blotting and providing transfer membranes.

10. The method of claim 1, wherein said analyte is mechanically added by an automated flow system or pipetting system.

11. The method of claim 1, wherein the enzyme or the enzyme-labelled biomolecule is present on an optionally fluorescently labelled particle having a diameter of 0.1 to 20 μm.

12. The method of claim 11, wherein the particles are subjected to a flow-cytometric detection method.

13. The method of claim 11, wherein the particles have a magnetic core.

14. The method of claim 12, wherein the particles have a magnetic core.

15. The method of claim 1, wherein the extent of the reaction caused by a catalase or peroxidase is quantified by means of the changes in the light absorption of the added reagent in the wavelength range between 300 and 450 nm.

16. The method of claim 1, wherein the extent of the reaction caused by a catalase or peroxidase is quantified by means of the changes in the luminescence of the added reagent by irradiating the solution with light of wavelengths between 300 and 450 nm and determining the change in the intensity or the decay time of the emission at wavelengths of >550 nm.

17. The method of claim 1, wherein self-fluorescence of the sample is suppressed by determining the luminescence of the reagent in such a manner that it is firstly irradiated with an excitation pulse lasting for <20 μs and the luminescence at >550 nm is not measured until after a delay phase of >1 μs.

18. The method of claim 1, wherein consumption of hydrogen peroxide caused by a catalase or peroxidase is monitored by means of the change in the luminescence-optical properties of the reagent per unit of time and this is related to a parameter to be determined.

19. The method of claim 1, wherein the luminescence-optical property is fluorescence.

* * * * *